United States Patent [19]
Hayashi et al.

[11] Patent Number: 5,523,437
[45] Date of Patent: Jun. 4, 1996

[54] TERTIARY PHOSPHINE COMPOUND AND TRANSITION METAL COMPLEX COMPRISING THE SAME AS LIGAND

[75] Inventors: Tamio Hayashi; Yasuhiro Uozumi, both of Sapporo; Kazunori Iwakura, Ibaraki; Isao Kurimoto, Oita; Masayoshi Minai, Moriyama, all of Japan

[73] Assignee: Sumitomo Chemical Co., Ltd., Osaka, Japan

[21] Appl. No.: 280,814

[22] Filed: Jul. 26, 1994

[30]   Foreign Application Priority Data

Oct. 7, 1993  [JP]  Japan ..................... 5-251635
    Feb. 9, 1994  [JP]  Japan ..................... 6-015341
    Feb. 10, 1994 [JP]  Japan ..................... 6-016760

[51] Int. Cl.$^6$ ................. C07F 15/00; C07F 7/08; C07F 9/02; C07C 2/02
[52] U.S. Cl. .............. 556/21; 556/23; 556/136; 556/138; 556/478; 556/487; 568/8; 568/16; 568/17; 585/527; 585/500
[58] Field of Search ............... 556/21, 23, 136, 556/138, 478, 487; 568/16, 17, 8; 585/527, 500

[56]       References Cited

FOREIGN PATENT DOCUMENTS 0503884   3/1992   European Pat. Off. .  9/1992  European Pat. Off. .

OTHER PUBLICATIONS

Hayashi et al., Synthesis, No. 5, pp. 526–532 (1994).
Uozumi et al., J. Am. Chem. Soc., vol. 113, No. 26, pp. 9887–9888 (1991).
Cram et al., J. Am. Chem. Soc., vol. 86, No. 24, pp. 5466–5477 (1964).
Uozumi et al. (1993) J. Org. Chem., 58, 1945–48.

*Primary Examiner*—Porfirio Nazario-Gonzales
*Attorney, Agent, or Firm*—Birch, Stewart, Kolasch & Birch

[57]            ABSTRACT

A tertiary phosphine compound of the formula (1):

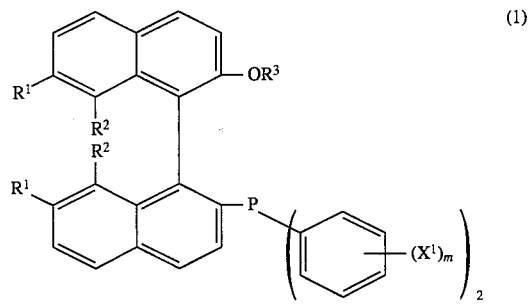

wherein $R^1$ and $R^2$ represent independently from each other a hydrogen atom or a methyl group, or together form $-CH=CH-CH=CH-$; $R^3$ is a hydrogen atom or a cycloalkyl group having 5 to 7 carbon atoms or a lower alkyl group which may be substituted with a halogen atom, a lower alkoxy group, a lower alkoxyalkoxy group or a phenyl group; $X^1$ is a halogen atom when both $R^1$ and $R^2$ are hydrogen atoms, or a hydrogen atom, a halogen atom, a lower alkyl group or a lower alkoxy group when at least one of $R^1$ and $R^2$ is not a hydrogen atoms; and m is an integer of 1 to 5, which is useful as a ligand of a transition metal complex that can catalyze various reactions.

17 Claims, No Drawings

TERTIARY PHOSPHINE COMPOUND AND TRANSITION METAL COMPLEX COMPRISING THE SAME AS LIGAND

BACKGROUND OF THE INVENTION

1. Field of the Invention

The present invention relates to a tertiary phosphine compound which is coordinated to various transition metals to form catalysts useful in asymmetric synthesis reactions and a transition metal complex comprising said phosphine compound as ligand.

2. Description of the Related Art

Hitherto, many reports have been made on transition metal catalysts used in the asymmetric synthesis reactions. It is well known that, among these catalysts, complexes of transition metals such as ruthenium, palladium and rhodium which comprise an optically active tertiary phosphine compound as a ligand have the excellent catalytic activities in the asymmetric syntheses (see JAPAN CHEMICAL SOCIETY Ed., ELEMENTS OF CHEMISTRY "KAGAKU SOSETSU") 32, "Chemistry of Organic Metal Complexes" (1982) 237–238).

Japanese Patent KOKAI Publication No. 17491/1993 describes that 2-diphenylphosphino-2'-methoxy-1,1'-binaphthyl having an axial asymmetry is an excellent ligand, and Japanese Patent KOKAI Publication No. 238964/1993 discloses an asymmetric formic acid reduction of a substituted allyl alcohol derivative using a catalyst having the above binaphthyl compound as a ligand. But, a selectivity and a yield of the reaction product can be still improved.

Japanese Patent KOKAI Publication No. 255353/1993 discloses an asymmetric hydrosilylation of a bicyclo[2.2.n]-compound with the above catalyst. However, the reaction tends to proceed explosively, while an asymmetric yield is decreased when a solvent is used to control the reaction. Therefore, the disclosed reaction is not necessarily satisfactory.

SUMMARY OF THE INVENTION

An object of the present invention is to provide a novel phosphine compound which can unexpectedly improve catalytic activities such as stereoselectivity or position selectivity and a conversion, which are unsatisfactory with the conventional catalysts.

Another object of the present invention is to provide industrially advantageous processes for preparing an optically active alpha-olefin compound and an optically active organic silicon compound, in which control of the reaction is easy.

According to a first aspect of the present invention, there is provided a tertiary phosphine compound of the formula (1):

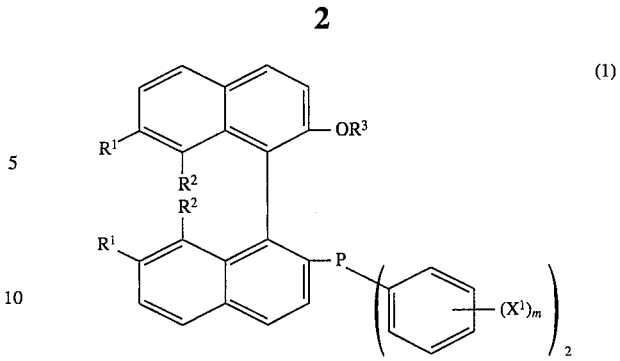

wherein $R^1$ and $R^2$ represent independently from each other a hydrogen atom or a methyl group, or together form a group of the formula:

$R^3$ is a hydrogen atom or a cycloalkyl group having 5 to 7 carbon atoms or a lower alkyl group which may be substituted with a halogen atom, a lower alkoxy group, a lower alkoxyalkoxy group or a phenyl group; $X^1$ is a halogen atom when both $R^1$ and $R^2$ are hydrogen atoms, or a hydrogen atom, a halogen atom, a lower alkyl group or a lower alkoxy group when at least one of $R^1$ and $R^2$ is not a hydrogen atoms; and m is an integer of 1 to 5.

According to a second aspect of the present invention, there is provided a transition metal complex comprising said tertiary phosphine compound (1) as a ligand.

According to a third aspect of the present invention, there is provided a process for producing an optically active alpha-olefin compound of the formula (2):

wherein $R^4$ is an alkyl group, a cycloalkyl group, an alkenyl group, a cycloalkenyl group or a substituted or unsubstituted phenyl group; $R^5$ is an alkyl group, a cycloalkyl group, an alkenyl group, a cycloalkenyl group, or a silicon atom which is substituted with a hydrogen atom, an alkyl group or a substituted or unsubstituted phenyl group; and the asterisk * indicates an asymmetric carbon comprising reducing a compound of the formula (3):

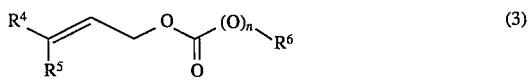

wherein $R^4$ and $R^5$ are the same as defined above; n is 0 or 1; and $R^6$ is a substituted or unsubstituted alkyl group or a substituted or unsubstituted phenyl group when n is 1, or a substituted or unsubstituted alkyl group, a substituted or unsubstituted phenyl group or a hydrogen atom when n is 0, with a reducing agent in the presence of a catalyst comprising a transition metal complex having a tertiary phosphine compound (1) as a ligand.

According to a fourth aspect of the present invention, there is provided a process for preparing a compound of the formula (4):

wherein $R^7$, $R^8$, $R^9$ and $R^{10}$ represent independently from each other an alkyl group, an alkenyl group, an alkynyl group, a cycloalkyl group, an aryl group, an aralkyl group, an alkoxy group or a hydrogen atom, or together form a ring; and $X^2$, $X^3$ and $X^4$ represent independently from each other a hydrogen atom, an alkyl group, an alkoxy group or a halogen atom comprising reacting a compound of the formula (5):

wherein $R^7$, $R^8$, $R^9$ and $R^{10}$ are the same as defined above with a silane compound of the formula (6):

wherein $X^2$, $X^3$ and $X^4$ are the same as defined above, in the presence of a catalyst comprising a transition metal complex having a tertiary phosphine compound (1) as a ligand.

DETAILED DESCRIPTION OF THE INVENTION

In the present invention, the lower alkyl group intends to mean an alkyl group having 1 to 4 carbon atoms, the lower alkoxy group intends to mean an alkoxy group having 1 to 4 carbon atoms, and the lower alkoxyalkoxy group intends to mean an alkoxyalkoxy group having 2 to 4 carbon atoms.

Examples of the substituent of the phenyl group are a methyl group, an ethyl group, a propyl group, a butyl group, an isopropyl group, a tert.-butyl group, a methoxy, group, an ethoxy group, a propoxy group, a butoxy group, a fluorine atom, a chlorine atom, a bromine atom, and the like.

Examples of the substituent of the alkyl group are a methoxy group, an ethoxy group, a propoxy group, a butoxy group, a fluorine atom, a chlorine atom, a bromine atom, and the like.

In the tertiary phosphine compound of the formula (1), specific examples of the cycloalkyl group having 5 to 7 carbon atoms as $R^3$ are a cyclopentyl group, a cyclohexyl group and the like.

Specific examples of the alkyl group which may be optionally substituted by a halogen atom, a lower alkoxy group, a lower alkoxyalkoxy group or a phenyl group are a methyl group, an ethyl group, a propyl group, a butyl group, an isopropyl group, a tert.-butyl group, a fluoromethyl group, a 2,2,2-trifluoroethyl group, a methoxymethyl group, a methoxyethoxymethyl group, a methoxypropyl group, a benzyl group, a diphenylmethyl group, a phenylpropyl group and the like. Among them, an alkyl group having 1 to 4 carbon atoms, a methoxymethyl group and a methoxyethoxymethyl group are preferred.

Specific examples of the $X^1$ are a methyl group, an ethyl group, a propyl group, a butyl group, a methoxy group, an ethoxy group, a propoxy group, a butoxy group, a fluorine atom, a chlorine atom, a bromine atom and the like. Positions and the number of the substituent $X^1$ are not critical. In particular, 4-substituted, 2,4-disubstituted and 2,4,6-substituted compounds are preferred.

The tertiary phosphine compound (1) of the present invention includes an optically active (+) and (−) isomers, and the present invention includes the (+) and (−) isomers and a racemic body.

Among the tertiary phosphine compound (I), a compound (Ia) corresponding to the formula (I) in which $R^1$ is other than a hydrogen atom may be prepared by the following reaction scheme:

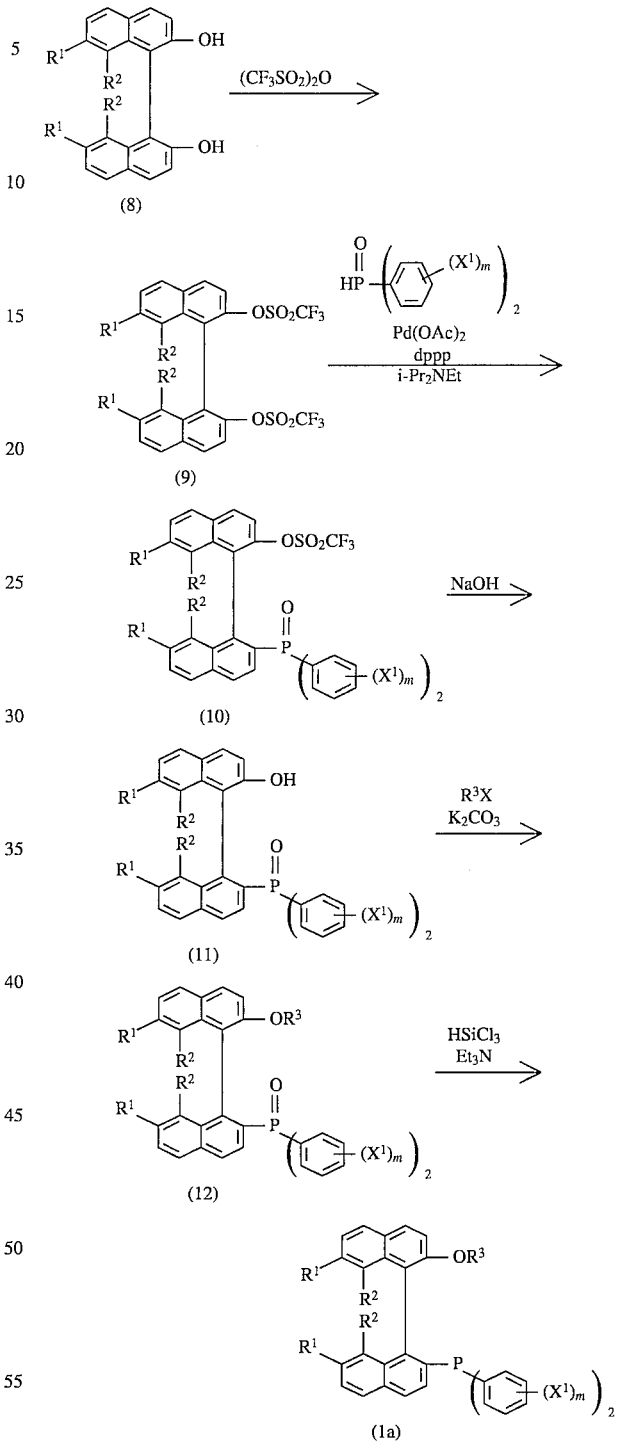

wherein $R^1$, $R^2$, $X^1$ and m are the same as defined above; and $R^3$ is a cycloalkyl group having 5 to 7 carbon atom or a lower alkyl group which may be substituted with a halogen atom, a lower alkoxy group, a lower alkoxyalkoxy group or a phenyl group.

That is, a compound (8) is reacted with trifluoromethanesulfonic anhydride in an amount of 2 to 20 moles, preferably 2 to 6 moles per one mole of the compound (8) in a solvent such as a hydrocarbon, a halogenated hydrocarbon or an ether in the presence of a base such as an aromatic amine or a tertiary amine in an amount of 2 to 20 moles, preferably 3 to 10 moles per one mole of the compound (8) at a temperature of −20° to +100° C., preferably from −10° to +50° C. for 1 to 10 hours to obtain a compound (9).

The obtained compound (9) is reacted with a diarylphosphine oxide in an amount of 1 to 10 moles, preferably 2 to 4 moles per one mole of the compound (9) in the presence of a base such as a tertiary amine in an amount of 1 to 20 moles, preferably 5 to 10 moles and a palladium-phosphine catalyst in an amount of 0.1 to 1 mole, preferably 0.4 to 0.6 mole per one mole of the compound (9) at a temperature of −20° to +100° C., preferably 0° C. to 50° C. for 1 to 20 hours to obtain a compound (10).

The compound (10) is then hydrolyzed in a solvent such as water, an alcohol, an ether or a mixture thereof in the presence of a base such as an alkali metal hydroxide in an amount of 1 to 20 moles, preferably 5 to 10 moles per one mole of the compound (10) at a temperature of −20° to +100° C., preferably 0° C. to 80° C. for 1 to 20 hours, followed by precipitation with an acid to obtain a compound (11).

The compound (11) is alkylated with an alkylating agent such as an alkyl halide in an amount of 1 to 20 moles, preferably 5 to 15 moles per one mole of the compound (11) in a polar solvent such as an alcohol, an ether or a ketone in the presence of a base such as an alkali carbonate in an amount of 1 to 20 moles, preferably 5 to 15 moles per one mole of the compound (11) at a temperature of −20° to 120° C., preferably +40° C. to 100° C. for 1 to 10 hours to obtain a compound (12).

Thereafter, the compound (12) is reduced with a reducing agent such as trichlorosilane in an amount of 1 to 50 moles, preferably 10 to 20 moles per one mole of the compound (12) in a solvent such as a hydrocarbon, a halogenated hydrocarbon or an ether in the presence of a base such as a tertiary amine in an amount of 1 to 100 moles, preferably 40 to 60 moles per one mole of the compound (12) at a temperature of −20° to +150° C. for 1 to 5 hours to obtain a compound (Ia).

Among the tertiary phosphine compound (I), a compound (Ib) corresponding to the formula (I) in which $R^1$ is a hydrogen atom may be prepared by the following reaction scheme:

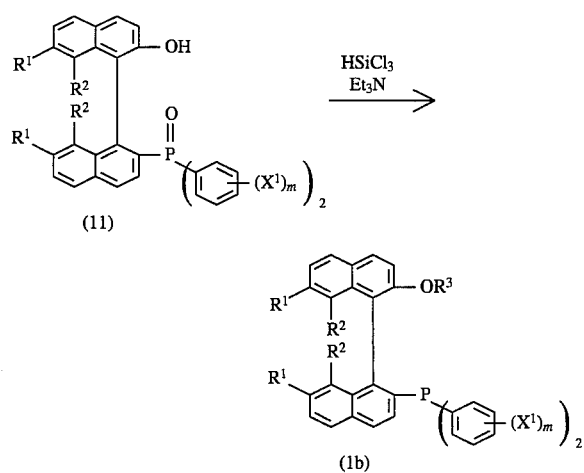

(11)

(Ib)

wherein $R^1$, $R^2$, $X^1$ and m are the same as defined above.

That is, the compound (11) is obtained in the same manners as in the above method. Then, the compound (11) is reduced with a reducing agent such as trichlorosilane in an amount of 1 to 50 moles, preferably 10 to 20 moles per one mole of the compound (11) in a solvent such as a hydrocarbon, a halogenated hydrocarbon or an ether in the presence of a base such as a tertiary amine in an amount of 1 to 100 moles, preferably 40 to 60 moles per one mole of the compound (11) at a temperature of −20° to +150° C. for 1 to 5 hours to obtain a compound (1b).

In the preparation of the compound (1), since the reactions of the respective steps proceed with maintaining a structure of the axial asymmetry of the substrates, an optically active compound (1) can be obtained as a final product when an optically active compound (8) is used as a starting compound. When a racemic compound (8) is used as a starting compound, a racemic compound (1) is obtained. According to the present invention, it is possible to obtain an optically active substance or a racemic substance according to the final use of the compound (1).

The tertiary phosphine compound (1) is coordinated on a transition metal as a ligand to form a complex.

Examples of the transition metal which forms such complex are palladium, rhodium, ruthenium, platinum and the like. When palladium is used, a reaction using the complex as a catalyst will proceed at a high stereoselectivity.

Among the complexes of the present invention, a palladium complex may be prepared by the method described in "Experimental Chemistry Lectures" (JIKKEN KAGAKU KOZA), 4th Edition, Vol. 18, "Organic Metal Complexes" (1991), page 393 (Maruzen), which comprises reacting dibenzonitrilepalladium dichloride with the tertiary phosphine compound (1) of the present invention to replace the ligand and isolating the resulting complex. Alternatively, the resulting complex may be used in a solution form in a further step without isolation.

Examples of transition metal salts to be used are allylpalladium chloride dimer, sodium tetrachloropalladate, dichlorobis(benzonitrile)palladium, ammonium tetrachloropalladate, and the like.

When the transition metal complex having the optically active substance of the tertiary phosphine compound (1) as the ligand is used as a catalyst in the asymmetric synthesis reaction such as an asymmetric reduction, a desired product can be obtained in a high yield and a high asymmetric yield.

For example, an optically active alpha-olefin compound of the formula (2):

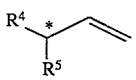

wherein $R^4$, $R^5$ and the asterisk * are the same as defined above is selectively prepared at a high yield and a high asymmetric yield by reducing a compound of the formula (3):

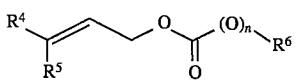

wherein n, $R^4$, $R^5$ and $R^6$ are the same as defined above with a reducing agent in the presence of a catalyst comprising the transition metal complex having the tertiary phosphine compound (1) as the ligand.

In the formulas (2) and (3), examples of $R^4$ are a methyl group, an ethyl group, a propyl group, a butyl group, an isopropyl group, a tert.-butyl group, a cyclopentyl group, a cyclohexyl group, a 3-pentenyl group, a 4-methyl-3-pentenyl group, a 2-cyclohexenyl group, a 3-cyclohexenyl group, a phenyl group, a p-tolyl group and the like, and examples of $R^5$ are a methyl group, an ethyl group, a propyl group, a butyl group, an isopropyl group, a tert.-butyl group, a cyclopentyl group, a cyclohexenyl group, a 3-pentenyl group, a 4-methyl-3-pentenyl group, a 2-cyclohexenyl group, a 3-cyclohexenyl group, a trimethylsilyl group, a triethylsilyl group, a phenyldimethylsilyl group and the like.

Examples of $R^6$ when n is 1 are a methyl group, an ethyl group, a propyl group, a butyl group, an isopropyl group, a tert.-butyl group, a benzyl group, a phenyl group, a p-tolyl group and the like. When n is 0, a hydrogen atom is a further example of $R^6$.

The tertiary phosphine compound according to the present invention is present both in the forms of the (+) isomer and the (–) isomer, and the present invention included the both (+) and (–) isomers. The reaction product prepared using the (+) isomer and that prepared using the (–) isomer are in the relationship of enantiomers. Then, either one of the (+) and (–) isomers is selected and used in accordance with a configuration of the desired alpha-olefin.

The compound (2) may be prepared from the compound (3) by, for example, the following method.

The compound (3) is reduced with a reducing agent in an amount of 1 to 20 moles, preferably 1 to 5 moles in a solvent such as a hydrocarbon, a halogenated hydrocarbon or an ether in the presence of the optically active tertiary phosphine compound (1) in an amount of 0.00001 to 0.1 mole, preferably 0.001 to 0.05 mole, a palladium complex such as tris(benzylideneacetone)(chloroform)dipalladium (0) and the like in an amount of 0.000001 to 0.05 mole, preferably 0.0001 to 0.02 mole and an organic salt such as 1,8-bis(dimethylamino)naphthalene in an amount of 1 to 10 moles, preferably 1 to 2 moles, all per one mole of the compound (3), at a temperature of –20° to +100° C., preferably –10° to +50° C. for 1 to 24 hours to obtain the compound (2).

Examples of the reducing agent are formic acid, ammonium formate, trimethylammonium formate, triethylammonium formate and the like.

In the above asymmetric reduction, when deuterated formic acid (DCOOD) is used in place of formic acid, an optically active alpha-olefin of the formula (7):

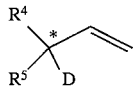
(7)

wherein $R^4$, $R^5$ and the asterisk * are the same as defined above is obtained.

In addition, the transition metal complex having the optically active substance of the tertiary phosphine compound (1) as the ligand has a high catalytic activity in an asymmetric hydrosilylation reaction and produces a desired product in a high yield and a high asymmetric yield.

For example, a compound of the formula (4):

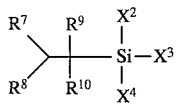
(4)

wherein $R^7$, $R^8$, $R^9$, $R^{10}$, $X^2$, $X^3$ and $X^4$ are the same as defined above is selectively prepared at a high yield and a high asymmetric yield by reacting a compound of the formula (5):

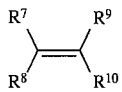
(5)

wherein $R^7$, $R^8$, $R^9$ and $R^{10}$ are the same as defined above with a silane compound of the formula (6):

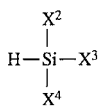
(6)

wherein $X^2$, $X^3$ and $X^4$ are the same as defined above, in the presence of a catalyst comprising the transition metal complex having the tertiary phosphine compound (1) as the ligand.

In the compound (5) used as the starting material in the above reaction, examples of the alkyl group for $R^7$ to $R^{10}$ are a methyl group, an ethyl group, a propyl group, a butyl group, an isopropyl group, a tert.-butyl group and the like, examples of the alkenyl group are a 2-butenyl group, a 3-pentenyl group and the like, examples of the alkynyl group are a 2-butynyl group, a 3-pentynyl group and the like, examples of the cycloalkyl group are a cyclopentyl group, a cyclohexyl group and the like, examples of the aryl group are a phenyl group, a naphthyl group and the like, examples of the aralkyl group are a benzyl group, a β-phenetyl group and the like, and examples of the alkoxy group are a methoxy group, an ethoxy group, a propoxy group and the like.

Examples of the compound in which two of $R^7$ to $R^{10}$ form a ring are dihydrofuran, cyclopentene, cyclohexene, norbornene, norbornadiene, bicyclo[2.2.2]octene, indene, dihydronaphthalene and the like. These compounds may be substituted by at least one alkyl group such as a methyl group, an ethyl group, a propyl group, a butyl group, an isopropyl group and a tert.-butyl group, at least one aryl group such as a phenyl group and a tolyl group, and at least one halogen atom such as a fluorine atom, a chlorine atom, a bromine atom and an iodine atom.

In the silane compound of the formula (6), examples of the alkyl group are a methyl group, an ethyl group, a propyl group and the like, examples of the alkoxy group are a methoxy group, an ethoxy group, a propoxy group and the like, and examples of the halogen atom are a chlorine atom, a bromine atom and the like.

The tertiary phosphine compound according to the present invention is present both in the forms of the (+) isomer and the (–) isomer, and the present invention included the both (+) and (–) isomers. The reaction product prepared using the (+) isomer and that prepared using the (–) isomer are in the relationship of enantiomers. Then, either one of the (+) and (–) isomers is selected and used in accordance with a configuration of the desired organic silicon compound.

The compound (7) may be prepared from the compound (3) by, for example, the following method.

The raw material olefin compound is added to a mixture of the transition metal complex in an amount of 0.001 to 1.0 mole, preferably 0.01 to 0.1 mole per one mole of the olefin compound and the optically active phosphine compound in an amount of 1 to 3 mole, preferably 2 moles per one mole of the transition metal complex in a solvent such as a hydrocarbon, a halogenated hydrocarbon or an ether, and 1 to 3 moles, preferably 1 to 1.2 moles of the silane compound such as trichlorosilane is reacted with one mole of the olefin compound at a temperature of –50° to +150° C., preferably –20° to +40° C. to obtain the optically active organic silicon compound. An order of the additions of the olefin compound and the silane compound may reversed, or they may be added at the same time. A pure compound can be isolated by distilling the reaction mixture.

The obtained optically active organic silicon compound can be converted to a corresponding alcohol with maintaining its configuration. For example, in the case of a trichlorosilyl compound, the silyl group is converted to a hydroxy group by reacting the compound with hydrogen peroxide in a mixed solvent of tetrahydrofuran and methanol in the presence of potassium bicarbonate.

As explained above, when the transition metal complex having the optically active substance of the tertiary phosphine compound (1) as the ligand is used as a catalyst for the asymmetric synthesis reaction such as the asymmetric reduction reaction and the asymmetric hydrosilylation reaction, the desired compound is selectively obtained at the high yield and the high asymmetric yield.

When the transition metal complex having, as the ligand, either one of the (+) and (−) isomers selected from the optically active substances of the tertiary phosphine compound (1) of the present invention is used as a catalyst, the product having the intended absolute configuration is selectively obtained by the asymmetric synthesis reaction.

Further, in the asymmetric silylation reaction, the reaction tends to proceed explosively in the conventional processes, and when the solvent is used to control the reaction, the asymmetric yield is decreased. But, when the tertiary phosphine compound (1) of the present invention is used, an induction time in the early period of the reaction is not found, the reaction does not proceed explosively, and the desired product is selectively obtained at the high yield and the high asymmetry yield.

PREFERRED EMBODIMENTS OF THE INVENTION

The present invention will be illustrated by the following Examples, which do not limit the scope of the present invention.

In the Examples, analyses were carried out using the following equipments:

Rotatory power: DIP-370 type (manufactured by Nippon Bunko Kogyo Co., Ltd.)

$^1$H-NMR spectrum: JNM-EX 270 type (270 MHx, manufactured by Nippon Denshi Co., Ltd.); internal standard: tetramethylsilane $^{31}$P-NMR spectrum: JNM-EX 270 type (109 Hz, manufactured by Nippon Denshi Co., Ltd.), external standard: phosphoric acid.

RAW MATERIAL SYNTHESIS 1 -(1)

Racemic 3,3'-dihydroxy-4,4'-biphenanthryl was synthesized according to the method disclosed in J. Chem. Soc., Chem. Commun., 1065 (1985), the disclosure of which is hereby incorporated by reference.

The racemic mixture (6.1 g) was subjected to optical resolution by HPLC (column: Sumichiral OA-2000 manufactured by Sumitomo Chemical Co., Ltd.; moving phase: n-hexane/1,2-dichloroethane/ethanol= 80/15/5 (by volume); UV-light detector: wavelength of 254 nm) to obtain (R)-(−)-3,3'-dihydroxy-4,4'-biphenanthryl and (S)-(+)-3,3'-dihydroxy-4,4'-biphenanthryl (each 2.9 g). Their optical purities were 99.9% ee and 99.5% ee, respectively.

RAW MATERIAL SYNTHESIS 1 -(2)

In the same manner as in Raw Material Synthesis 1-(1), 2-hydroxy-7-methylnaphthalene was oxidized by the conventional method to obtain racemic 2,2'-dihydroxy-7,7'-dimethyl-1,1'-binaphthyl. Racemic mixture (2.5 g) was subjected to optical resolution by HPLC (column: Sumichiral OA-2000 manufactured by Sumitomo Chemical Co., Ltd.; moving phase: n-hexane/1,2-dichloroethane/ethanol=100/20/1 (by volume); UV-light detector: wavelength of 254 nm) to obtain (R)-(+)-2,2'-dihydroxy-7,7'-dimethyl-1,1'-binaphthyl and (S)-(−)-2,2'-dihydroxy-7,7'-dimethyl-1,1'-binaphthyl (each 0.5 g). Their optical purities were 97.4% ee and 95.4% ee, respectively.

EXAMPLE 1 -(1)

In a solution of (R)-(−)-3,3'-dihydroxy-4,4'-biphenanthryl (1.91 g, 4.89 mmol) and pyridine (1.97 ml, 24.4 mmol) in dichloromethane cooled with ice, trifluoromethanesufonic anhydride (5.50 g, 19.5 mmol) was dropwise added. After stirring the mixture at 0° C. for one hour, the solvent was evaporated off. The residue was diluted with ethyl acetate (50 ml) and washed with 5% hydrochloric acid, a saturated aqueous solution of sodium hydrogencarbonate and a saturated aqueous solution of sodium chloride successively. The organic layer was dried over anhydrous sodium sulfate, and the solvent was evaporated off to obtain a crude product.

Then, the crude product was purified by silica gel column chromatography (developing phase: dichloromethane) to obtain (R)-(−)-3,3'-bis(trifluoromethanesulfonyloxy)-4,4'-biphenanthryl (3.15 g). Yield, 100%. Melting point: 162.5° to 163.0° C. Rotatory power: $[\alpha]_D^{22}$=−18.2 (C=0.4, CHCl$_3$). Elementary analysis: $C_{30}H_{16}O_6S_2F_6$ Calculated: C, 55.38%; H, 2.47% Found: C, 55.58%; H, 2.66%.

EXAMPLE 1 -(2)

Under a nitrogen atmosphere, (R)-(−)-3,3'-bis(trifluoromethanesulfonyloxy)-4,4'-biphenanthryl (3.15 g, 4.84 mmol), diphenylphosphine oxide (2.93 g, 14.5 mmol), palladium acetate (433 mg, 1.93 mmol) and 1,4-bis(diphenylphosphino)propane (796 mg, 1.93 mmol) were added to a solution of diisopropylethylamine (5.2 g, 40.1 mmol) in dimethylsulfoxide (35 ml), and the mixture was stirred at 150° C. for 10 hours. After cooling, the solvent was evaporated off under reduced pressure, and the residue was diluted with ethyl acetate and washed with dilute hydrochloric acid and a saturated aqueous solution of sodium hydrogencarbonate successively. The organic layer was dried over anhydrous magnesium sulfate, and the solvent was evaporated off to obtain a crude product.

Then, the crude product was purified by silica gel column chromatography (developing phase: n-hexane/ethyl acetate= 1/1) to obtain (R)-(+)-3-diphenylphosphinyl-3'-trifluoromethanesulfonyloxy-4,4'-biphenanthryl (2.41 g). Yield, 70%. Melting point: 254.0° to 255.0° C. Rotatory power: $[\alpha]_D^{20}$=+15.0 (C=0.82, CHCl$_3$). $^{31}$P-NMR (CDCl$_3$): δ(ppm)=29.6 (s). Elementary analysis: $C_{41}H_{26}O_4SF_3P$ Calculated: C, 70.08%; H, 3.72% Found: C, 70.04%; H, 3.88%.

EXAMPLE 1 -(3)

(R)-(+)-3-Diphenylphosphinyl-3'-trifluoromethanesulfonyloxy-4,4'-biphenanthryl (985 mg, 1.40 mmol) was dissolved in a mixed solvent of methanol (2.5 ml) and 1,4-dioxane (5 ml). To the solution, a 3N aqueous solution of sodium hydroxide (5 ml) was added, and the mixture was stirred at room temperature for 9 hours. While cooling with ice, conc. hydrochloric acid was added to the reaction mixture to acidify it (pH of about 1). Then, the mixture was extracted with ethyl acetate (twice). The organic layer was dried over anhydrous magnesium sulfate, and the solvent was evaporated off to obtain a crude product.

Then, the crude product was purified by silica gel column chromatography (developing phase: ethyl acetate) to obtain (R)-(−)-3-diphenylphosphinyl-3'-hydroxy-4,4'-biphenanthryl (794 mg). Yield, 99%. Rotatory power: :$[\alpha]_D^{20}$=−63.4 (C=0.55, CH$_2$Cl$_2$). $^1$H-NMR (CDCl$_3$): δ(ppm)=6.26–8.07 (m, 26H), 8.55 (brs, 1H). $^{31}$P-NMR (CDCl$_3$): δ(ppm)=32.6 (s).

EXAMPLE 1 -(4)

In a suspension of (R)-(−)-3-diphenylphosphinyl-3'-hydroxy-4,4'-biphenanthryl (792 mg, 1.38 mmol) and anhydrous potassium carbonate (1.79 g, 13.02 mmol)in acetone (30 ml), methyl iodide (1.85 g, 13.02 mmol) was added and the mixture was refluxed for 5 hours. After cooling, the reaction mixture was filtrated through a sellaite filter and washed with diethyl ether. From the combined filtrate and diethyl ether phase, the solvents were evaporated off to obtain a crude product.

Then, the crude product was purified by silica gel column chromatography (developing phase: n-hexane/ethyl acetate= ⅓) to obtain (R)-(+)-3-diphenylphosphinyl-3'-methoxy-4,4'-biphenanthryl (781 mg). Yield, 97%. Melting point: 218.0° to 219.5° C. Rotatory power: :$[\alpha]_D^{20}$=+85.8 (C=0.50, CHCl$_3$). $^1$H-NMR (CDCl$_3$): δ(ppm)=3.43 (s, 3H), 6.63–7.90 (m, 26H). $^1$P-NMR (CDCl$_3$): δ(ppm)=29.2 (s). Elementary analysis: C$_{41}$H$_{29}$PO$_2$ Calculated: C, 84.23%; H, 4.99% Found: C, 83.97%; H, 4.87%.

EXAMPLE 1-(5)

Under a nitrogen atmosphere, in a solution of (R)-(+)-3-diphenylphosphinyl-3'-methoxy-4,4'-biphenanthryl (185 mg, 0.31 mmol) and triethylamine (1.23 g, 12.1 mmol) in toluene (5 ml), trichlorosilane (617 mg, 4.55 mmol) was added at 0° C., and then heated to 110° C. and stirred at that temperature for 10 hours. After cooling to room temperature, the reaction mixture was diluted with diethyl ether, and a small amount of a saturated aqueous solution of sodium hydrogencarbonate was added to stop the reaction. Then, the reaction mixture was filtrated through a sellaite filter, and washed with diethyl ether. From the combined filtrate and diethyl ether phase, the solvents were evaporated off to obtain a crude product.

Then, the crude product was purified by silica gel column chromatography (developing phase: n-hexane/dichloromethane=1/1) to obtain (R)-(+)-3-diphenylphosphino-3'-methoxy-4,4'-biphenanthryl (161 mg). Yield, 91%. Melting point: 209.5° to 210.0° C. Rotatory power: :$[\alpha]_D^{20}$=+271.6 (C=1.29, CHCl$_3$). $^1$H-NMR (CDCl$_3$): δ(ppm)=3.07 (s, 3H), 6.58–8.12 (m, 26H). $^{31}$P-NMR (CDCl$_3$): δ(ppm)=−12.3 (s). Elementary analysis: C$_{41}$H$_{29}$PO Calculated: C, 86.59%; H, 5.14% Found: C, 86.45%; H, 5.37%.

EXAMPLE 2-(1)

In a solution of (R)-(+)-2,2'-dihydroxy-7,7'-dimethyl-1,1'-binaphthyl (1.54 g, 4.89 mmol) and pyridine (1.97 ml, 24.4 mmol) in dichloromethane which was cooled with ice, trifluoromethanesufonic anhydride (5.50 g, 19.5 mmol) was dropwise added. After stirring the mixture at 0° C. for one hour, the solvent was evaporated off. The residue was diluted with ethyl acetate (50 ml) and washed with 5% hydrochloric acid, a saturated aqueous solution of sodium hydrogencarbonate and saturated aqueous solution of sodium chloride successively. The organic layer was dried over anhydrous sodium sulfate, and the solvent was evaporated off to obtain a crude product.

Then, the crude product was purified by silica gel column chromatography (developing phase: dichloromethane) to obtain (R)-(+)-2,2'-bis(trifluoromethanesulfonyloxy)-7,7'-dimethyl-1,1'-binaphthyl (2.49 g). Yield, 99%. Rotatory power: :$[\alpha]_D^{22}$=+156.9 (C=0.98, CHCl$_3$). $^1$H-NMR (CDCl$_3$): δ(ppm)=2.31 (s, 6H), 7.08 (s, 2H), 7.41 (d, J=8.3 Hz, 2H), 7.53 (d, J=8.9 Hz, 2H), 7.90 (d, J=8.3 Hz, 2H), 8.08 (d, J=8.9 Hz, 2H). Elementary analysis: C$_{24}$H$_{16}$O$_6$S$_2$F$_6$ Calculated: C, 56.02%; H, 3.13% Found: C, 56.18%; H, 3.09%.

EXAMPLE 2-(2)

Under a nitrogen atmosphere, (R)-(+)-2,2'-bis(trifluoromethanesulfonyloxy)-7,7'-dimethyl-1,1'-binaphthyl (2.49 g, 4.84 mmol), diphenylphosphine oxide (2.93 g, 14.5 mmol), palladium acetate (433 mg, 1.93 mmol) and 1,4-bis(diphenylphosphino)propane (796 mg, 1.93 mmol) were added to a solution of diisopropylethylamine (5.2 g, 40.1 mmol)in dimethylsulfoxide (35 ml), and the mixture was stirred at 150° C. for 10 hours. After cooling, the solvent was evaporated off under reduced pressure, and the residue was diluted with ethyl acetate and washed with dilute hydrochloric acid and a saturated aqueous solution of sodium hydrogencarbonate successively. The organic layer was dried over anhydrous magnesium sulfate, and the solvent was evaporated off to obtain a crude product.

Then, the crude product was purified by silica gel column chromatography (developing phase: n-hexane/ethyl acetate= 1/1) to obtain (R)-(−)-2-diphenylphosphinyl-2'-trifluoromethanesulfonyloxy-7,7'-dimethyl-1,1'-binaphthyl (2.20 g). Yield, 72%. Rotatory power: :$[\alpha]_D^{25}$=−73.8 (C=0.98, CHCl$_3$). $^1$H-NMR (CDCl$_3$): δ(ppm)=2.13 (s, 3H), 2.24 (s, 3H), 6.69 (s, 1H), 6.93 (s, 1H), 7.22–7.98 (m, 18H). Elementary analysis: C$_{35}$H$_{26}$O$_4$SF$_3$P Calculated: C, 66.66%; H, 4.16% Found: C, 66.74%; H, 41.3%.

EXAMPLE 2-(3)

(R )-(−)-2-Diphenylphosphinyl-2'-trifluoromethanesulfonyloxy-7,7'-dimethyl-1,1'-binaphthyl (883 mg, 1.40 mmol) was dissolved in a mixed solvent of methanol (2.5 ml) and 1,4-dioxane (5 ml). To the solution, a 3N aqueous solution of sodium hydroxide (5 ml) was added, and the mixture was stirred at room temperature for 9 hours. While cooling with ice, conc. hydrochloric acid was added to the reaction mixture to acidify it (pH of about 1). Then, the mixture was extracted with ethyl acetate (twice). The organic layer was dried over anhydrous magnesium sulfate, and the solvent was evaporated off to obtain a crude product.

Then, the crude product was purified by silica gel column chromatography (developing phase: ethyl acetate) to obtain (R)-(+)-2-diphenylphosphinyl-2'-hydroxy-7,7'-dimethyl-1,1'-binaphthyl (691 mg). Yield, 99%. Rotatory power: :$[\alpha]_D^{23}$=+83.1 (C=0.84, CHCl$_3$). $^1$H-NMR (CDCl$_3$): δ(ppm)= 2.12 (s, 3H), 2,17 (s, 3H), 6.14 (s, 1H), 6.68–7.96 (m, 19H), 8.72 (s, 1H). Elementary analysis: C$_{34}$H$_{27}$O$_2$P Calculated: C, 81.91%; H, 5.46% Found: C, 81.82%; H, 5.41%.

EXAMPLE 2-(4)

In a suspension of (R)-(+)-2-diphenylphosphinyl-2'-hydroxy-7,7'-dimethyl-1,1'-binaphthyl (688 mg, 1.38 mmol) and anhydrous potassium carbonate (1.79 g, 13.02 mmol) in acetone (30 ml), methyl iodide (1.85 g, 13.02 mmol) was added, and the mixture was refluxed for 5 hours. After cooling, the reaction mixture was filtrated through a sellaite filter and washed with diethyl ether. From the combined filtrate and diethyl ether phase, the solvents were evaporated off to obtain a crude product.

Then, the crude product was purified by silica gel column chromatography (developing phase: n-hexane/ethyl acetate= ⅓) to obtain (R)-(−)-2-diphenylphosphinyl-2'-methoxy-7,7'-dimethyl-1,1'-binaphthyl (781 mg). Yield, 98%. Rotatory power: $[\alpha]_D^{22}$=−127.2 (C=0.91, CHCl$_3$). $^1$H-NMR (CDCl$_3$): δ(ppm)=2.12 (s, 3H), 2.21 (s, 3H), 3.59 (s, 3H), 6.48 (s, 1H), 6.87 (s, 1H), 6.92–7.98 (m, 18H). Elementary analysis: C$_{35}$H$_{29}$O$_2$P Calculated: C, 82.01%; H, 5.70% Found: C, 82.12%; H, 5.66%.

EXAMPLE 2-(5)

Under a nitrogen atmosphere, in a solution of (R)-(−)-2-diphenylphosphinyl-2'-methoxy-7,7'-dimethyl-1,1'-binaphthyl (159 mg, 0.31 mmol) and triethylamine (1.23 g, 12.1 mmol) in toluene (5 ml), trichlorosilane (617 mg, 4.55 mmol) was added at 0° C., and then heated to 110° C. and stirred at that temperature for 10 hours. After cooling to room temperature, the reaction mixture was diluted with diethyl ether, and a small amount of a saturated aqueous solution of sodium hydrogencarbonate was added to stop the reaction. Then, the reaction mixture was filtrated through a sellaite filter, and washed with diethyl ether. From the combined filtrate and diethyl ether phase, the solvents were evaporated off to obtain a crude product.

Then, the crude product was purified by silica gel column chromatography (developing phase: n-hexane/dichloromethane=1/1) to obtain (R)-(−)-2-diphenylphosphino-2'-methoxy-7,7'-dimethyl-1,1'-binaphthyl (142 mg). Yield, 92%. Rotatory power: $[\alpha]_D^{23}$=−118.3 (C=0.79, CHCl$_3$). $^1$H-NMR (CDCl$_3$): δ(ppm)=2.13 (s, 3H), 2.25 (s, 3H), 3.42 (s, 3H), 6.65 (s, 1H), 7.02 (s, 1H), 7.05–7.95 (m, 18H). Elementary analysis: C$_{35}$H$_{29}$OP Calculated: C, 84.65%; H, 5.89% Found: C, 84.58%; H, 5.95%.

EXAMPLE 3

In the same manner as in Example 2 except that (R)-(+)-2,2'-dihydroxy-1,1'-binaphthyl in place of (R)-(+)-2,2'-dihydroxy-7,7'-dimethyl-1,1'-binaphthyl, and di(4-chlorophenyl)phosphine in place of diphenylphosphine oxide, the reactions were carried out to obtain (R)-2-methoxy-2'-di(4-chlorophenyl)phosphino-1,1'-binaphthyl. Total yield, 49%. Rotatory power: $[\alpha]_D^{22}$=+82.2 (C=0.96, CHCl$_3$). $^1$H-NMR (CDCl$_3$): δ(ppm)= 3.41 (s, 3H), 6.84–8.01 (m, 20H).

EXAMPLE 4-(1)

In a Schlenk's tube, (R)-(+)-3-diphenylphosphino-3'-methoxy-4,4'-biphenanthryl prepared in Example 1 (6.24 mg, 0.011 mmol) and tris(dibenzylideneacetone)(chloroform)dipalladium (0) (2.6 mg, 0.0025 mmol) were charged, and dioxane was added under a nitrogen atmosphere. To the mixture cooled on an ice bath, 1,8-bis(dimethylamino)naphthalene (128.6 mg, 0.60 mmol) and formic acid (52.5 mg, 1.14 mmol) were added in this order. At the same temperature, geranylmethyl carbonate (104.5 mg, 0.49 mmol) was added, and the mixture was stirred at 20° C. for 17 hours. The reaction mixture was diluted with pentane and washed with water, and the organic layer was dried over anhydrous magnesium sulfate and filtrated through a mass of silica gel. From the filtrate, the solvent was evaporated off under reduced pressure to obtain (S)-3,7-dimethyl-1,6-octadiene as a colorless oil (68.0 mg). Yield, >99%. Rotatory power: $[\alpha]_D^{20}$=+8.1 (C=1.6, CHCl$_3$). $^1$H-NMR (CDCl$_3$): δ(ppm)=0.98 (d, J=7.0 Hz, 3H), 1.27–1.36 (m, 2H), 1.60 (s, 3H), 1.67 (s, 3H), 1.96 (q, J=7.0 Hz, 2H), 2.12 (heptet, J=7 Hz, 1H), 4.88–4.99 (m, 2H), 5.05–5.15 (m, 1H), 5.70 (ddd, J=17.1, 10.1 and 7.0 Hz, 1H).

The optical purity of the product was determined by converting it to a diamide while maintaining the configuration by the following method and subjecting it to LC (liquid chromatography) analysis using a column for isolating optical isomers.

EXAMPLE 4-(2)

(S)-3,7-Dimethyl-1,6-octadiene (85% ee) (61 mg, 0.44 mmol) was dissolved in a mixture of water (20 ml) and tert.-butanol (10 ml). To the solution cooled with ice, potassium permanganate, (185 mg, 1.17 mmol), sodium metaperiodate (1.46 g, 6.86 mmol) and potassium carbonate (366 mg, 2.64 mmol) were added. To the reaction mixture, a 3N aqueous solution of sodium hydroxide was added to adjust pH to 8, followed by stirring at room temperature for 2 hours. While cooling with ice, conc. hydrochloric acid was added to the reaction mixture to adjust pH to 1. Then, sodium nitrite was added till the color of solution was changed from reddish brown to yellow, and the reaction mixture was extracted with diethyl ether. The organic layer was extracted with a 3N aqueous solution of sodium hydroxide twice, and thereafter, the aqueous layer was washed with diethyl ether once. To the aqueous layer, conc. hydrochloric acid was added to adjust pH to 1, and then the aqueous layer was extracted with diethyl ether three times. After drying the organic layer over anhydrous magnesium sulfate, the solvent was evaporated off under reduced pressure to obtain (S)-2-methylpentane dicarboxylic acid as a pale yellow oil (38 mg). Yield, 58%. Optical purity, 85% ee. Rotatory power: $[\alpha]_D^{20}$=+17.4 (C=1.63, CHCl$_3$). $^1$H-NMR (CDCl$_3$): δ(ppm)=1.23 (d, J=7.0 Hz, 3H), 1.8–2.1 (m, 2H), 2.4–2.7 (m, 3H), 9.0–10.5 (br, 2H).

EXAMPLE 4-(3)

(S)-2-Methylpentane dicarboxylic acid (85% ee) (10 mg, 0.68 mmol) was dissolved in tetrahydrofuran (THF) (0.5 ml). To the solution, 1-(3-dimethylaminopropyl)-3-ethylcarbodiimide (30 μl) and aniline (15 mg, 0.16 mmol) were added, followed by stirring at 40° C. for one hour. After adding conc. hydrochloric acid, the reaction mixture was extracted with ethyl acetate. Then, the solvent was evaporated off to obtain a crude product.

Then, the crude product was purified by silica gel column chromatography (developing phase: n-hexane/ethyl acetate= 1/1) to obtain (S)-2-methylpentane dicarboxylic acid dianilide as a while solid.

An excessive ratio of enantiomers of the diamide body was measured using HPLC (column: Sumichiral OA-4100 manufactured by Sumitomo Chemical Co., Ltd.) (developing phase: n-hexane/1,2-dichloroethane/ethanol=50/15/1; UV-light detector: wavelength of 254 nm) and was 85% ee. Rotatory power: $[\alpha]_D^{20}$=+10.0 (C=0.32, CHCl$_3$). $^1$H-NMR (CDCl$_3$): δ(ppm)=1.26 (d, J=7.0 Hz, 3H), 1.89–2.10 (m, 2H), 2.43–2.49 (m, 3H), 2.61–2.69 (m, 2H), 7.06–7.14 (m, 2H), 7.13–7.35 (m, 4H), 7.49–7.57 (m, 4H), 8.05 (brs, 2H).

COMPARATIVE EXAMPLE 1

In the same manner as in Example 4 except that (R)-(+)-2-diphenylphosphino-2'-methoxy-1,1'-binaphthyl was used in place of (R)-(+)-3-diphenylphosphino-3'-methoxy- 4,4'-diphenanthryl in Example 4-(1), the reaction was carried out to obtain (S)-3,7-dimethyl-1,6-octadiene in the yield of 99%, but its optical purity was 76% ee.

EXAMPLE 5

In the same manner as in Example 4 except that nerylmethyl carbonate was used in place of geranylmethyl carbonate in Example 4-(1), the reaction was carried out to obtain (R)-3,7-dimethyl-1,6-octadiene in the yield of 99% or higher, and its optical purity was 82% ee.

EXAMPLE 6

In the same manner as in Example 4 except that trans-3-cyclohexyl-2-butenylmethyl carbonate was used in place of geranylmethyl carbonate in Example 4-(1), the reaction was carried out to obtain (R)-3-cyclohexyl-1-butene in the yield of 96%, and its optical purity was 85% ee. Rotatory power: $[\alpha]_D^{24}$ +4.2 (C=1.9, CHCl$_3$). $^1$H-NMR (CDCl$_3$): δ(ppm)= 0.98 (d, J=6.9 Hz, 3H), 0.92–1.78 (m, 11H) 1.91–2.04 (m, 1H), 4.88–4.94 (m, 2H), 5.68 (m, 1H).

EXAMPLE 7

In the same manner as in Example 4 except that trans-3-phenyl-2-butenylmethyl carbonate was used in place of geranylmethyl carbonate in Example 4-(1), the reaction was carried out to obtain (R)-3-phenyl-1-butene in the yield of 91%, and its optical purity was 64% ee. Rotatory power: $[\alpha]_D^{25}$=−2.2 (C=0.7, CHCl$_3$). $^1$H-NMR (CDCl$_3$): δ(ppm)= 1.39 (d, J=6.8 Hz, 3H), 2.48 (quintet, J=6.8 Hz, 1H), 5.04 (dd, J=10.5 and 16.0 Hz, 2H), 6.02 (ddd, J=6.8, 10.5 and 16.0 Hz, 1H), 7.19–7.34 (m, 5H).

EXAMPLE 8

In the same manner as in Example 4 except that deuterated formic acid (DCOOD) in place of formic acid (HCOOH), the reaction was carried out to obtain (D)-3,7-dimethyl-3-$^2$H-1,6-octadiene in the yield of 93%, and its optical purity was 84% ee. Rotatory power: $[\alpha]_D^{20}$=+10.4 (C=2.0, CHCl$_3$). $^1$H-NMR (CDCl$_3$): δ(ppm)=0.98 (s, 3H), 1.25–1.34 (t, J=6.8 Hz, 2H), 1.60 (s, 3H), 1.68 (s, 3H), 1.96 (q, J=6.8 Hz, 2H), .4.90 (ddd, J=17.1, 9.9 and 2.0 Hz, 2H), 5.05–5.15 (m, 1H), 5.70 (dd, J=17.1 and 9.9 Hz, 1H).

EXAMPLE 9

In the same manner as in Example 6 except that deuterated formic acid (DCOOD) in place of formic acid (HCOOH), the reaction was carried out to obtain (D)-3-cyclohexyl-3-$^2$H-1-butene in the yield of 94%, and its optical purity was 85% ee. Rotatory power: $[\alpha]_D^{24}$=+6.0 (C=1.0, CHCl$_3$). $^1$H-NMR (CDCl$_3$): δ(ppm)= 0.95 (s, 3H), 0.88–1.78 (m, 11H), 1.91–2.04 (m, 1H), 4.88–4.94 (m, 2H), 5.65–5.76 (m, 1H).

EXAMPLE 10-(1)

In a Schlenk's tube, (R)-(+)-3-diphenylphosphino-3'-methoxy-4,4'-biphenanthryl prepared in Example 1 (10.2 mg, 0.018 mmol) and tris(dibenzylideneacetone)(chloroform)dipalladium (0) (4.7 mg, 0.0045 mmol) were charged, and dioxane (1 ml) was added under a nitrogen atmosphere. To the mixture cooled on an ice bath, 1,8-bis(dimethylamino)naphthalene (77.1 mg, 0.36 mmol) and formic acid (30.1 mg, 0.65 mmol) were added in this order. At the same temperature, cis-3-phenyl-3-triethylsilyl-2-propenylmethyl carbonate (90.3 mg, 0.29 mmol) was added, and the mixture was stirred at 20° C. for 33 hours. The reaction mixture was diluted with pentane and washed with water, and the organic layer was dried over anhydrous magnesium sulfate and filtrated through a mass of silica gel. From the filtrate, the solvent was evaporated off under reduced pressure to obtain (R)-3-phenyl-3-triethylsilyl-1-propene as a colorless oil (66.3 mg). Yield, 95%. Optical purity, 88% ee.

The optical purity was determined by converting the product to the compound known from the literature and measuring its optical purity from a rotatory power and the LC analysis according to the procedure of Example 10-(2).

Rotatory power: $[\alpha]_D^{20}$=−55.2 (C=1.0, PhH). $^1$H-NMR (CDCl$_3$): δ(ppm)=0.53 (q, J=7.5 Hz, 6H), 0.89 (t, J=7.5 Hz, 9H), 3.17 (d, J=9.9 Hz, 1H), 4.49–5.04 (m, 2H), 6.26 (ddd, J=9.9, 10.5 and 16.8 Hz, 1H), 7.12–7.19 (m, 2H), 7.26–7.35 (m, 3H). Elementary analysis: $C_{12}H_{24}O_3Si$ Calculated: C, 77.51%; H, 10.41% Found: C, 77.90%; H, 10.74%.

EXAMPLE 10-(2)

To a solution of (R)-3-phenyl-3-triethylsilyl-1-propene prepared in Example 10-(1) (16.8 mg,0.072 mmol) in methylene chloride (2 ml), pivalic aldehyde (6.4 mg, 0.074 mmol) and a 1M solution of titanium tetrachloride in methylene chloride (75 μl, 0.075 mmol) were added at −78° C., and the mixture was stirred for 5 minutes. After adding water, the reaction mixture was extracted with methylene chloride and the organic layer was dried over anhydrous magnesium sulfate. After distilling the solvent off, the residue was purified by silica gel column chromatography (developing phase: methylene chloride) to obtain (R)-trans-2,2-dimethyl-6-phenyl-5-hexene-3-ol (10.3 mg). Yield, 72%.

The product had the rotatory power $[\alpha]_D^{20}$ of +39.5 (C=0.6, CCl$_4$). The product was found to be the (R)-isomer from that (R)-(+)-trans-2,2-dimethyl-6-phenyl-5-hexene-3-ol with the optical purity of 91% ee had the rotatory power $[\alpha]_D^{20}$ of +44.7 (C=0.5, CCl$_4$) which is described in J. Org. Chem., 48, 281 (1983).

Judging from the already reported stereochemistry of the reaction between an optically active allylsilane such as (R)-3-phenyl-3-triethylsilyl-1-propene and aldehyde, the absolute configuration of (R)-3-phenyl-3-triethylsilyl-1-propene was determined as (R).

Obtained (R)-trans-2,2-dimethyl-6-phenyl-5-hexene-3-ol was converted to 3,5-dinitrophenyl carbamate by the conventional method, and subjected to the HPLC analysis using a column for isolating optical isomers to find that its optical purity was 88% ee.

EXAMPLE 11

In the same manner as in Example 10-(1) except that cis-3-triethylsilyl-2-butenylmethyl carbonate was used in place of cis-3-phenyl-3-triethylsilyl-2-propenylmethyl carbonate, the reaction was carried out to obtain (S)-3-triethylsilyl-1-butene in the yield of 90%, and its optical purity was 72% ee.

The configuration of obtained (S)-3-triethylsilyl-1-butene was determined to be the (S) isomer from that the same compound having the optical purity of 49% ee had the rotatory power $[\alpha]_D^{20}$ of −27.2 (C=3.5, PhH) which is described in J. Org. Chem., 51, 3773 (1986).

As described in Example 4-(2), obtained (S)-3-triethylsilyl-1-butene was converted to 3,5-dinitrophenyl carbamate by the conventional method, and subjected to the HPLC analysis using a column for isolating optical isomers to find that its optical purity was 72% ee.

Rotatory power: :[α]$_D^{20}$=−38.1 (C=0.65, PhH). $^1$H-NMR (CDCl$_3$): δ(ppm)=0.55 (q, J=7.9 Hz, 6H), 0.96 (t, J=7.9 Hz, 9H), 1.09 (d, J=6.9 Hz, 3H), 1.77 (quintet, J=6.9 Hz, 1H), 4.85 (m, 2H), 5.93 (m, 1H).

EXAMPLE 12-(1)

(R)-2-Methoxy-2'-di(4-chlorophenyl)phosphino-1,1'-binaphthyl prepared in Example 3 (7.93 mg, 14.78 mmol) and allylpalladium chloride dimer (1.35 mg, 3.69 μmol=7.38 μmol of palladium) were dissolved in toluene (6.95 g). In the solution, norbornene (6.95 g, 73.81 mmol) was added. After adding trichlorosilane (12.00 g, 88.59 mmol) at 0° C., the mixture was warmed to room temperature, followed by stirring at room temperature for 12 hours. Thereafter, from the reaction mixture, the solvent was evaporated off at 100° C. under reduced pressure of 1 Torr to obtain (1S, 2S, 4R)-2-trichlorosilylnorbornane (16.41 g). Isolation yield, 97%.

The optical purity of the product was determined by converting its trichlorosilyl group to a hydroxy group while maintaining the configuration by the following methods, and it is subjected to GC analysis using a column for isolating optical isomers.

EXAMPLE 12-(2)

Potassium hydrogencarbonate (21.48 g, 214.5 mmol) was added to a mixture of THF (30 ml) and methanol (30 ml) to form a suspension. To the suspension, (1S, 2S, 4R)-2-trichlorosilylnorbornane (16.41 g, 71.47 mmol) was dropwise added while stirring and cooling with ice. After stirring the mixture for 2 hours, 30% aqueous hydrogen peroxide (55 ml) was added, followed by stirring at 50° C. for 24 hours. After cooling to room temperature, the reaction mixture was extracted with diethyl ether, and the organic layer was washed with a saturated aqueous solution of sodium chloride and dried over anhydrous sodium sulfate, followed by evaporating the solvent off to obtain (1S, 2S, 4R)-2-norbornanol (5.60 g). Isolation yield, 70%. This was subjected to the GC analysis using a column for isolating isomers to find that its optical purity was 95% ee. Rotatory power: :[α]$_D^{20}$= −3.0 (C=2.82, CHCl$_3$). $^1$H-NMR (CDCl$_3$): δ(ppm)= 0.88–1.73 (m, 9H), 2.09 (d, J=4.4 Hz, 1H), 2.31 (s, 1H), 3.82 (d, J=6.8 Hz, 1H).

COMPARATIVE EXAMPLE 2

In the same manner as in Example 12-(1) except that (R)-(+)-2-diphenylphosphino-2'-methoxy-1,1'-binaphthyl in place of (R)-2-methoxy-2'-di(4-chlorophenyl)phosphino-1, 1'-binaphthyl, the reaction was carried out to obtain (1S, 2S, 4R)-2-trichlorosilylnorbornane in the isolation yield of 95%, and its optical purity was 89% ee.

COMPARATIVE EXAMPLE 3

In the same manner as in Comparative Example 2 except that no solvent was used, reaction heat was suddenly generated after several minutes from the start of the reaction, and the control of the reaction was difficult.

What is claimed is:
1. A tertiary phosphine compound of the formula (1):

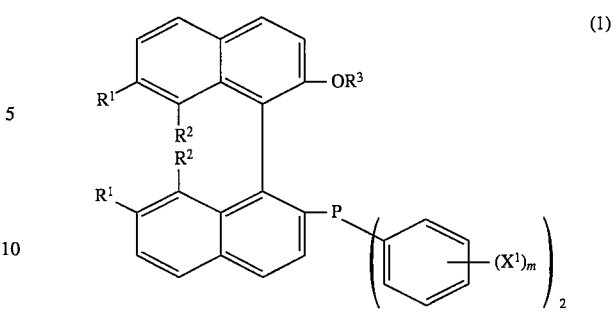

wherein $R^1$ and $R^2$ represent independently from each other a hydrogen atom or a methyl group, or together form a group of the formula:

$R^3$ is a hydrogen atom or a cycloalkyl group having 5 to 7 carbon atoms or a lower alkyl group which may be substituted with a halogen atom, a lower alkoxy group, a lower alkoxyalkoxy group or a phenyl group; $X^1$ is a a chlorine or bromine atom and m is 1 when both $R^1$ and $R^2$ are hydrogen atoms, or a hydrogen atom, a halogen atom, a lower alkyl group or a lower alkoxy group and m is an integer of 1 to 5 when at least one of $R^2$ and $R^2$ is not a hydrogen atom.

2. A transition metal complex comprising a transition metal selected from the transition metals of the groups 8, 9 and 10 and a tertiary phosphine compound (1) according to claim 1, as a ligand.

3. An optically active substance of a tertiary phosphine compound (1) according to claim 1.

4. A transition metal complex comprising a transition metal selected from the transition metals of the groups 8, 9 and 10 and an optically active substance of a tertiary phosphine compound (1) according to claim 3, as a ligand.

5. A process for producing an optically active alpha-olefin compound of the formula (2):

wherein $R^4$ is an alkyl group, a cycloalkyl group, an alkenyl group, a cycloalkenyl group or a substituted or unsubstituted phenyl group; $R^5$ is an alkyl group, a cycloalkyl group, an alkenyl group, a cycloalkenyl group, or a silicon atom which is substituted with a hydrogen atom, an alkyl group or a substituted or unsubstituted phenyl group; and the asterisk * indicates an asymmetric carbon comprising reducing a compound of the formula (3):

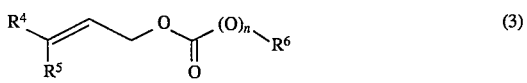

wherein $R^4$ and $R^s$ are the same as defined above; n is 0 or 1; and $R^6$ is a substituted or unsubstituted alkyl group or a substituted or unsubstituted phenyl group when n is 1, or a substituted or unsubstituted alkyl group, a substituted or unsubstituted phenyl group or a hydrogen atom when n is 0, with a reducing agent in the presence of a catalyst comprising a transition metal complex as recited in claim 2.

6. The process according to claim 5, wherein said transition metal is palladium, and said reducing agent is formic acid or its salt.

7. The process according to claim 5, wherein said transition metal is palladium, and said reducing agent is deuterated formic acid or its salt, provided that at least one of $R^4$ and $R^5$ in the formula (3) is not a hydrogen atom.

8. An optically active alpha-olefin of the formula (7):

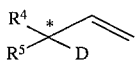 (7)

wherein $R^4$ is an alkyl group, a cycloalkyl group, an alkenyl group, a cycloalkenyl group or a substituted phenyl group; $R^5$ is an alkyl group, a cycloalkyl group, an alkenyl group, a cycloalkenyl group, or a silicon atom which is substituted with a hydrogen atom, an alkyl group or a substituted or unsubstituted phenyl group; and the asterisk * indicates an asymmetric carbon.

9. A process for preparing a compound of the formula (4):

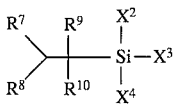 (4)

wherein $R^7$, $R^8$, $R^9$ and $R^{10}$ represent independently from each other an alkyl group, an alkenyl group, an alkynyl group, a cycloalkyl group, an aryl group, an aralkyl group, an alkoxy group or a hydrogen atom, or together form a ring; and $X^2$, $X^3$ and $X^4$ represent independently from each other a hydrogen atom, an alkyl group, an alkoxy group or a halogen atom, comprising reacting a compound of the formula (5):

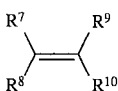 (5)

wherein $R^7$, $R^8$, $R^9$ and $R^{10}$ are the same as defined above with a silane compound of the formula (6):

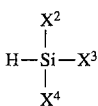 (6)

wherein $X^2$, $X^3$ and $X^4$ are the same as defined above, in the presence of a catalyst comprising a transition metal complex comprising a transition metal selected from the transition metals of the groups 8, 9 and 10 and having a tertiary phosphine compound (1) according to claim 1 as a ligand.

10. The process according to claim 9, wherein said transition metal complex is a palladium complex.

11. The process according to claim 9, wherein said silane compound (6) is trichlorosilane.

12. The process according to claim 9, wherein said compound (5) is norbornene.

13. The transition metal complex according to claim 2, wherein said transition metal is a metal selected from the group consisting of palladium, rhodium, ruthenium and platinum.

14. The transition metal complex according to claim 4, wherein said transition metal is a metal selected from the group consisting of palladium, rhodium, ruthenium and platinum.

15. The tertiary phosphine compound of claim 1, wherein said lower alkyl group has 1 to 4 carbon atoms, said lower alkoxy group has 1 to 4 carbon atoms, and said lower alkoxyalkoxy group has 2 to 4 carbon atoms.

16. The process of claim 5, wherein $R^4$ is selected from the group consisting of a methyl group, an ethyl group, a propyl group, a butyl group, an isopropyl group, a tert.-butyl group, a cyclopentyl group, a cyclohexyl group, a 3-pentenyl group, a 4-methyl-3-pentenyl group, a 2-cyclohexenyl group, a 3-cyclohexenyl group, a phenyl group, and a p-tolyl group; and wherein $R^5$ is selected from the group consisting of a methyl group, an ethyl group, a propyl group, a butyl group, an isopropyl group, a tert.-butyl group, a cyclopentyl group, a cyclohexenyl group, a 3-pentenyl group, a 4-methyl-3-pentenyl group, a 2-cyclohexenyl group, a 3-cyclohexenyl group, a trimethylsilyl group, a triethylsilyl group, and a phenyldimethylsilyl group; and wherein $R^6$ is selected from the group consisting of a methyl group, an ethyl group, a propyl group, a butyl group, an isopropyl group, a tert.-butyl group, a benzyl group, a phenyl group, and a p-tolyl group.

17. The optically active alpha-olefin of claim 8, wherein $R^4$ is selected from the group consisting of a methyl group, an ethyl group, a propyl group, a butyl group, an isopropyl group, a tert.-butyl group, a cyclopentyl group, a cyclohexyl group, a 3-pentenyl group, a 4-methyl-3-pentenyl group, a 2-cyclohexenyl group, a 3-cyclohexenyl group, and a p-tolyl group; and wherein $R^5$ is selected from the group consisting of a methyl group, an ethyl group, a propyl group, a butyl group, an isopropyl group, a tert.-butyl group, a cyclopentyl group, a cyclohexenyl group, a 3-pentenyl group, a 4-methyl-3-pentenyl group, a 2-cyclohexenyl group, a 3-cyclohexenyl group, a trimethylsilyl group, a triethylsilyl group, and a phenyldimethylsilyl group.

* * * * *